United States Patent [19]

Umezawa et al.

[11] 4,259,319

[45] Mar. 31, 1981

[54] ANTIBIOTIC AUROMOMYCIN, AND PROCESS FOR PRODUCTION THEREOF

[75] Inventors: Hamao Umezawa; Tomio Takeuchi; Masaaki Ishizuka, all of Tokyo; Kiyoshi Watanabe, Akashi; Toshiaki Yamashita, Kakogawa; Noriyuki Naoi; Takayoshi Hidaka, both of Kobe, all of Japan

[73] Assignees: Kanegafuchi Chemical Industry Company, Limited, Osaka; Zaidan Hojin Biseibutsu Kagaku Kenkyu Kai, Tokyo, both of Japan

[21] Appl. No.: 936,835

[22] Filed: Aug. 25, 1978

[30] Foreign Application Priority Data

Aug. 25, 1977 [JP] Japan ............................. 52-102323

[51] Int. Cl.³ ............................................ H61K 35/00
[52] U.S. Cl. ................................... 424/117; 435/169

[58] Field of Search ................... 424/117; 195/80 R; 435/169

[56] References Cited

U.S. PATENT DOCUMENTS 3,595,954   7/1971   Umezawa et al. ................ 424/117

*Primary Examiner*—Jerome D. Goldberg
*Attorney, Agent, or Firm*—Armstrong, Nikaido, Marmelstein & Kubovcik

[57] ABSTRACT

A new antibiotic designated as auromomycin is prepared from the culture broth of *Streptomyces macromomyceticus*, a macromomycin-producing strain, as yellow crystals. Auromomycin is recovered in pure form from the culture broth by using hydrophobic chromatography with Octyl Sephalose CL-4B or Phenyl Sepharose CL-4B.

1 Claim, 3 Drawing Figures

4,259,319

ANTIBIOTIC AUROMOMYCIN, AND PROCESS FOR PRODUCTION THEREOF

BACKGROUND OF THE INVENTION

The present inventors obtained a purified anti-tumor antibiotic effective against transplanted tumors from a filtrate of the culture broth of *Streptomyces macromomyceticus*, a macromomycin-producing strain, as yellow crystal which have evidently different properties from those of macromomycin (U.S. Pat. No. 3,595,954).

SUMMARY OF THE INVENTION

This invention relates to auromomycin, a new antibiotic effective against transplanted tumors. More specifically, the invention relates to auromomycin, a new antibiotic, which is isolated from the culture broth filtrate of *Streptomyces macromoceticus*, a macromomycin-producing strain, as yellow crystals and has evidently different properties from those of macromomycin and other proteinous anti-tumor substances.

The present inventors obtained a purified antibacterial active substance from a filtrate of the culture broth of *Streptomyces macromomyceticus* by a combination of various purifying procedures such as salting-out, ion-exchange chromatography, adsorption chromatography, and gel filtration chromatography, and isolated it as yellow crystals by adding ammonium sulfate to this solution. The ultraviolet absorption spectrum of this active substance shows a maximum absorption at 270~275 mμ and 350~360 mμ, and a valley appears at 280 mμ and 350 mμ in its optical rotatory dispersion spectrum. This substance strongly inhibits both Gram-positive bacteria and Gram-negative bacteria, and in tiny amounts, inhibits the growth of L1210 leukemia, ascites sarcoma 180 and Ehrlich ascites carcinoma in mice. From this fact, the present substance has been found to have clearly different properties from those of macromomycin (U.S. Pat. No. 3,595,954) and other substances of the polypeptide structure. This antibiotic in the form of a high-molecular-weight polypeptide has been identified as a new substance and termed auromomycin.

DETAILED DESCRIPTION

Figure 1:
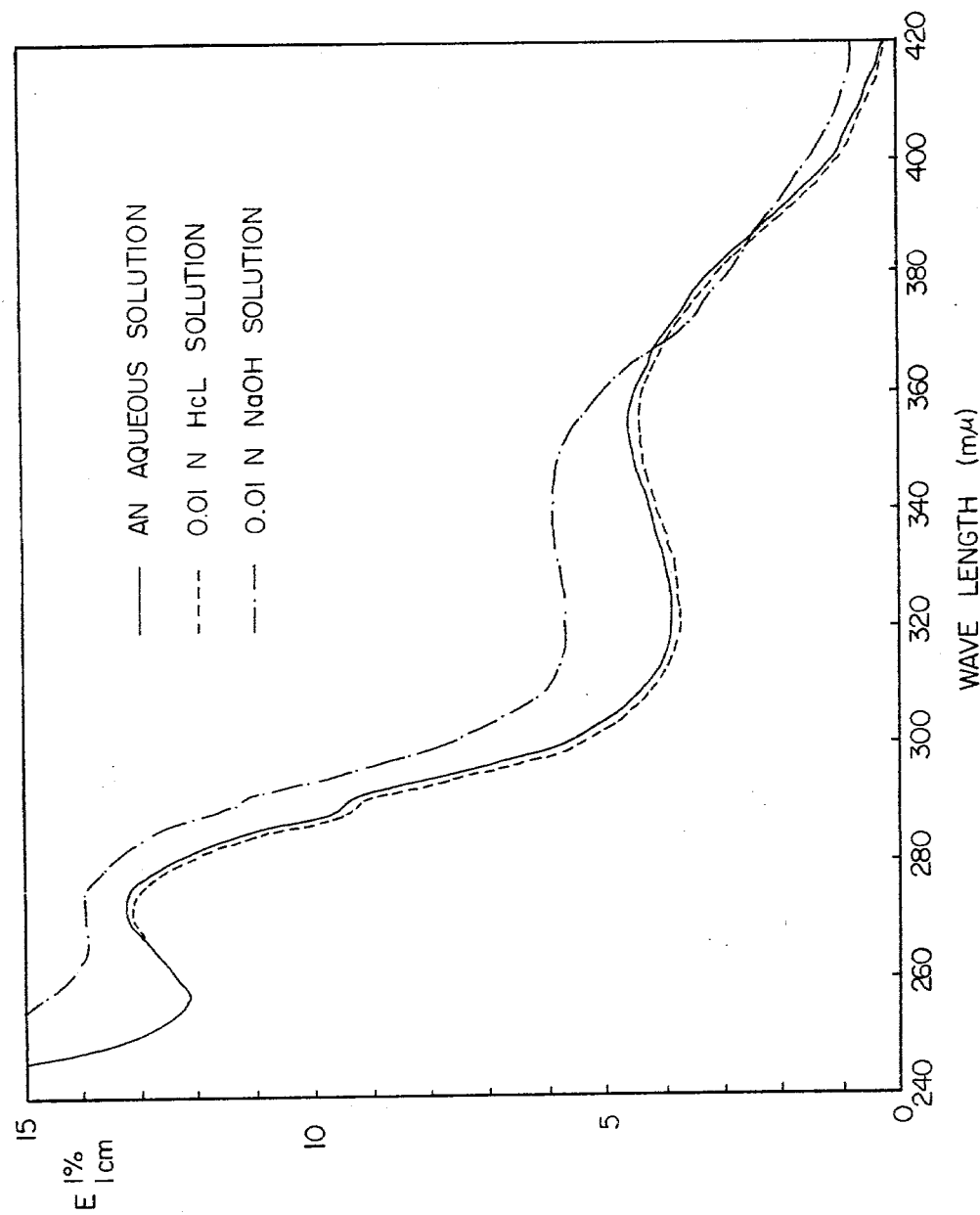
FIG. 1 shows the ultraviolet and visible region absorption spectral curves of auromomycin in aqueous solution, 0.01 N sodium hydroxide solution, and 0.01 N hydrochloric acid solution.

The microorganism used in the preparation of the compound of this invention has the same microbilogical properties (i.e., in morphology, physiological properties, and growth conditions in various culture media) as *Streptomyces macromomyceticus* described in U.S. Pat. No. 3,595,954. It has been deposited with the American Type Culture Collection and designated as *Streptomyces macromomyceticus* ATCC 29816. Accordingly, strains used in the present invention include *Streptomyces macromomyceticus* ATCC 29816 and all its mutants. Furthermore, the strains, as referred to herein, include all species belonging to the genus Streptomyces and mutants thereof having the ability to produce auromomycin. In producing the present antibiotic, *Streptomyces macromomyceticus* is cultivated in a culture medium containing known nutrient sources which ordinary microorganisms can utilize. For example, commercially available saccharides such as glucose, glycerol, starch, dextrin, sucrose, maltose, and others, and oils and fats can be used. As nitrogen sources, organic materials such as soybean powder, cotton seed residues, meat extract, peptone, dry yeast, yeast extract, corn steep liquor, peanut powder, casein and casamino acid, and ammonium salts, nitrate salts and urea can be used. If desired, inorganic salts such as sodium chloride, potassium chloride, phosphates and heavy metal salts may be added. Also, silicone oils, soybean oil, and polyalkylene glycol-type antifoamers can be added as desired to inhibit foaming during fermentation. Sterilization of the culture medium is performed by ordinary steam sterilization. After the sterilization, the suitable pH of the culture medium is 5 to 8. Submerged aerobic culture is most suitable as a method of cultivation as is the case with the production of antibiotics generally practiced. The cultivation is carried out at 20° to 35° C., but usually, temperatures of 25° to 30° C. are desirable. According to this method, the production of auromomycin reaches a maximum concentration in 2 to 4 days in shaking culture and aerated submerged culture.

Auromomycin is determined by a cylinder plate method using *Sarcina lutea* PCI 1001. A nutrient agar for a seed layer and a base layer contains 0.6% of peptone, 0.3% of yeast extract, 0.15% of meat extract, 0.1% of glucose and 1.5% of agar, and its pH is adjusted to 6.7. Agar medium for base layer (16 ml) is dispensed into each of the Petri dishes with inside diameter of about 90 mm and 8 ml of the inoculated agar for seed layer is spread on it. The inoculated agar is prepared by mixing 0.5 ml of the suspension of a microorganism to 100 ml of the nutrient agar for seed layer.

Auromomycin produced by the cultivation is present mainly in the liquid portion, and a cultivation liquor containing auromomycin is separated from solids of the cells by a known method such as filtration or centrifufal separation. As required, hydrogen peroxide may be added in order to maintain the culture broth in an aerobic condition during the separation of the cultivation liquor. To the resulting filtrate, a known salting-out agent such as ammonium sulfate is added. The precipitate containing auromomycin which is obtained by salting out is centrifugally separated, or collected by filtration after adding a filtration aid such as diatomaceous earth. To facilitate the recovery of the precipitate obtained by salting out, a coagulant, such as ferric sulfate, ferric chloride or aluminum sulfate, may be added. When the addition of the coagulant results in a drastic change in the pH of the solution, a neutralizing agent such as sodium carbonate, calcium carbonate, monosodium phosphate or disodium phosphate may be added immediately before the addition of the coagulant to maintain the pH of the solution at 5 to 8. The resultant precipitate is dissolved in water or a suitable buffer such as a tris-HCl buffer or a phosphate buffer. The salting out may be repeated.

After desalting by using a cellophane tube or a ultrafiltration, or directly, the aqueous solution containing auromomycin is passed through a known ion exchange resin such as Cl-types of strong base-type ion exchange resins such as Dowex 1 (a trademark of Dow Chemical Company) or Amberlite IRA-400 (a trademark of Rohm & Hass Company) or Cl-types of weak base-type ion exchange resins such as Amberlite IR-45 or Amberlite IRA-93, or a known adsorbent such as activated carbon, hydroxyapatite, or high-flow supercell to cause the adsorption of much impurities thereby to permit a passage of auromomycin.

The resulting auromomycin-containing solution is concentrated by ultrafiltration, etc., and purified by gel filtration, for example by chromatography on Sephadex G-50 (a trademark of Pharmacia Fine Chemicals, Sweden) or Sephadex G-75 (a trademark of Pharmacia Fine Chemicals, Sweden). Then auromomycin is caused to be absorbed to ion-exchange Sephadex or ion-exchange cellulose and eluted with a neutral salt such as sodium chloride or a suitable buffer such as a tris-HCl buffer or a phosphate buffer whereby the auromomycin can be further purified.

The present inventors have found that in addition to methods frequently used heretofor for the purification of proteins, such as salting out, gel filtration or ion exchange as described above, the so-called hydrophobic chromatography using Octyl Sepharose CL-4B (a trademark of Pharmacia Fine Chemicals, Sweden) or Phenyl Sepharose CL-4B (a trademark of Pharmacia Fine Chemicals, Sweden) is an effective method for the purification of auromomycin. A salt such as ammonium sulfate or sodium chloride is added to the auromomycin-containing solution in a high concentration of the range which does not cause the precipitation of auromomycin. After dissolving the solution obtained is passed through a column filled with Octyl Sephalose CL-4B or Phenyl Sepharose CL-4B to cause the adsorption of auromomycin. The column is eluted with an aqueous solution of ammonium sulfate having the same concentration and gradually with aqueous solutions of ammonium sulfate having lower ammonium sulfate concentrations. Alternatively, the column may be eluted with an ammonium sulfate solution containing an organic solvent such as methanol, ethanol or ethylene glycol, or with water containing any one of these organic solvents. By utilizing the difference in resin adsorptive power in this manner, it is possible to separate impure proteins which have not been able to be separated by conventional purifying procedures such as salting out, gel filtration, ion exchange, etc., and obtain a fraction containing auromomycin in a high concentration. The hydrophobic chromatography can be applied to a filtrate of the fermentation broth of auromomycin, a solution in each stage of a purifying process by a combination of salting out, gel filtration, ion exchange, etc., or an aqueous solution of a purified powder obtained by these purifying methods. When this method is applied to an auromomycin-containing solution in the early stage of purification which contains large amounts of impure proteins, most of the impure proteins having a different affinity for the resin are removed. Macromomycin and auromomycin can be separated by means of hydrophobic chromatography using Octyl Sepharose CL-4B or Phenyl Sepharose CL-4B.

Through the column is passed 30~40% saturated aqueous ammonium sulfate solution containing macromomycin and auromomycin. The column is eluted with an aqueous ammonium sulfate solution of the same concentration as above, whereby auromomycin is eluted. Then, the column is eluted with an aqueous solution of ammonium sulfate of gradiently decreasing concentrations, whereby macromomycin is eluted. Hence, this method has an extremely high purifying efficiency. After this treatment, highly pure auromomycin can be obtained by further purifying the fraction containing auromomycin by a combination of salting out, gel filtration, ion exchange, etc.

When salts are contained in the purified auromomycin-containing solution finally obtained, the salts can be removed by chromatography on Sephadex G-25 and Sephadex G-50, ultrafiltration, dialysis, etc. to obtain an aqueous solution containing only the purified auromomycin.

Repetition of the various chromatographic processes described above is useful for removing tiny amounts of impurities.

By lophilizing the auromomycin-containing solution obtained by purification through various combinations of the above mehods, a yellow powder can be obtained. Alternatively, yellow crystals can be precipitated by adding a known salting-out agent such as ammonium sulfate to the auromomycin solution and allowing the mixture to stand in a cold dark place.

That the resulting auromomycin is a homogeneous substance is proven by a single band in disc poly-acrylamide gel electrophoresis, a sharp, single peak in column chromatography on Sephadex G-50, a single peak in isoelectric point electrophoresis using LKB Ampholine 8101 (pH of the carrier ampholite is in the range of 5 to 8), and a single peak in a sedimentation pattern of ultracentrifugal analysis. The characteristics of auromomycin will be described below.

1. Characteristics

It is obtained as yellow plate-like crystals. It is weakly acidic at an isoelectric point of pH 5.4. It is readily soluble in water, but scarcely soluble in organic solvents such as methanol, ethanol, acetone and ethyl acetate.

2. Melting point (decomposition point)

It does not show any definite melting point nor decomposition point. It browns and carbonizes while foaming, and carbonizes completely at 260° C.

3. Optical rotation $[\alpha]_D^{20}$ measured in 1 % aqueous solution is $-280°$.

4. Ultraviolet absorption spectrum

As shown in FIG. 1, the spectrum shows an ultraviolet absorption maximum at 273 mμ ($E_{1\ cm}^{1\%}$ 13.3) and 357 mμ ($E_{1\ cm}^{1\%}$ 4.6) in aqueous solution, at 270~274 mμ ($E_{1\ cm}^{1\%}$ 14.0) and 340 mμ ($E_{1\ cm}^{1\%}$ 5.9) in a 0.01 N sodium hydroxide solution, and 272 mμ ($E_{1\ cm}^{1\%}$ 13.2) and 356 mμ ($E_{1\ cm}^{1\%}$ 4.4) in a 0.01 N hydrochloric acid solution. In any of these solutions, the ultraviolet absorption spectrum has a shoulder at 290 mμ.

5. Infrared absorption spectrum

Figure 2:
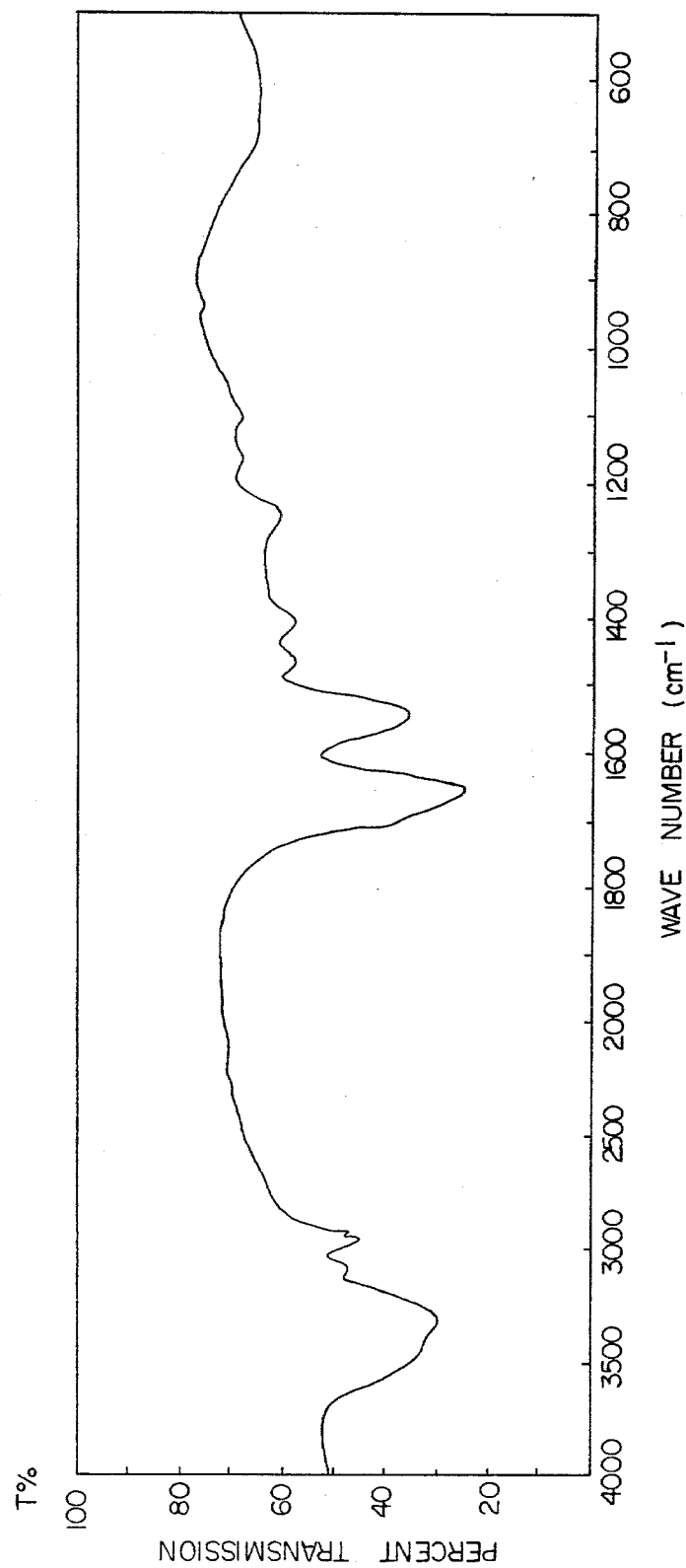
FIG. 2 shows the infrared absorption spectral curve of auromomycin determined by using a potassium bromide tablet.

The infrared absorption spectrum of auromomycin measured on a potassium bromide tablet is shown in FIG. 2. Wavenumbers ($cm^{-1}$) at which main absorption bands exist are 3300, 2980, 1650, 1540, 1460, 1400, and 1240. A slight absorption is shown at 3100, 1160, 1100 and 930 $cm^{-1}$.

6. Optical rotatory dispersion spectrum

Figure 3:
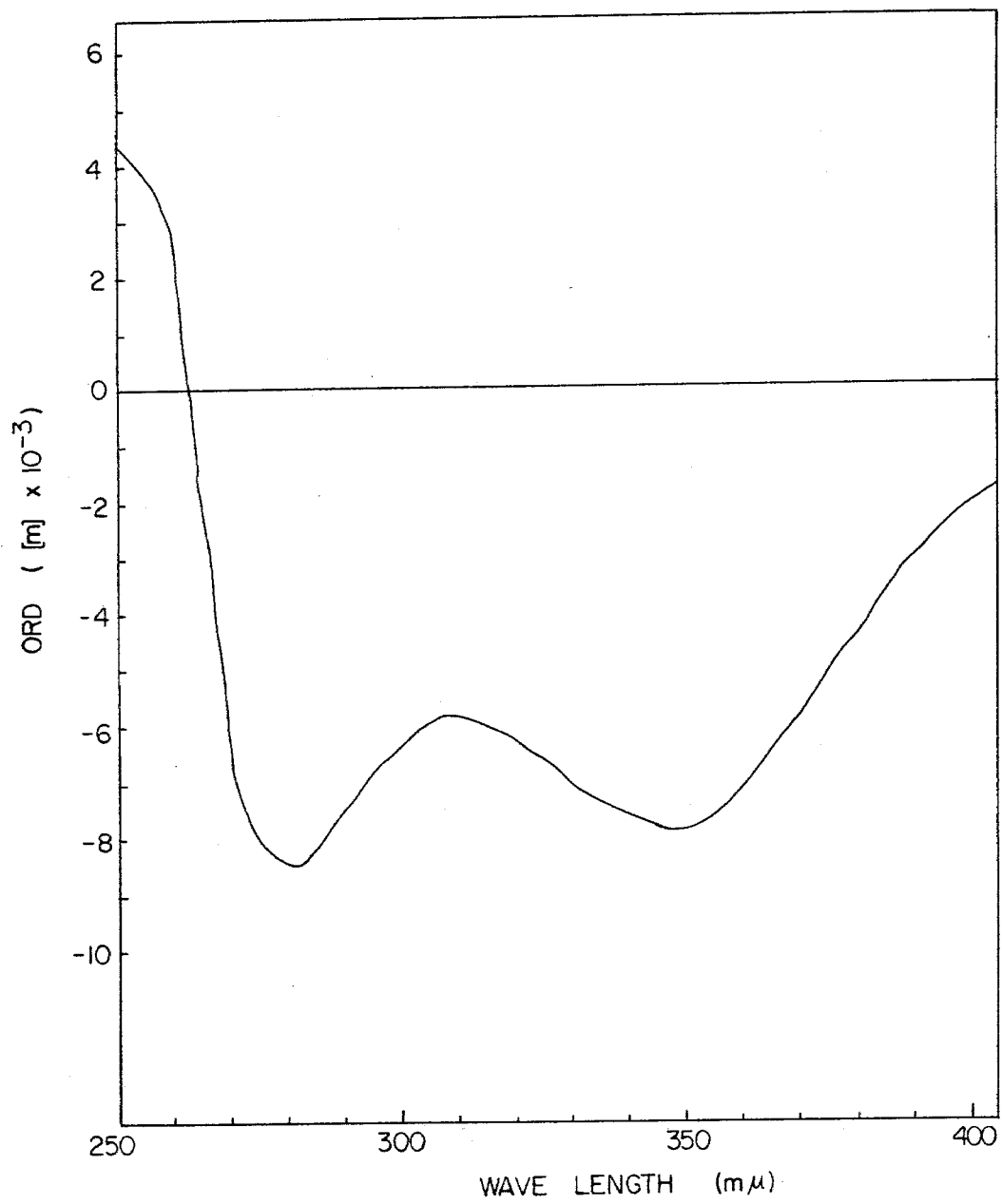
FIG. 3 shows the optical rotatory dispersion spectral curve of auromomycin in an aqueous solution (2 mg/ml).

The optical rotatory dispersion spectrum of auromomycin measured in an aqueous solution (2 mg/ml) is shown in FIG. 3. A valley is shown at 280 mμ and 350 mμ.

7. Color reactions

Auromomycin decolorizes a potassium permanganate solution, is positive in Folin-Lowry, xanthoproteic, Ehrlich, biuret, and ninhydrin reactions, and is negative in phenol sulfuric acid, anthrone, orcinol, Elson-Morgan and Molisch reactions.

8. Molecular weight

Its molecular weight is 12,500 as demonstrated from the fact that in a gel filtration method using Sephadex G-50, it is eluted in the same fraction as cytochrome C (molecular weight 12,500).

9. Elementary analysis

Carbon 47.06%, hydrogen 6.62%, nitrogen 14.66%, sulfur 3.25%, oxygen 25.80%. It does not contain halogen and phosphorus.

10. Molecular formula

From its molecular weight calculated from the result of gel filtration, $(C_{39}H_{65}O_{16}N_{10}S)_{12-14}$ is given as an inferred formula.

11. Constituent amino acids

It was dissolved in 6 N hydrochloric acid and hydrolyzed at 110° C. for 22 hours. The results are shown in Table 1. The analytical value of cystine is that obtained after oxidation with performic acid, and the analytical value of tryptophan is that obtained after hydrolysis with barium hydroxide.

TABLE 1

The composition of amino acids

| Amino acid | % by weight |
|---|---|
| Aspartic acid | 8.04 |
| Threonine | 15.29 |
| Serine | 7.44 |
| Glutamic acid | 8.79 |
| Proline | 4.26 |
| Glycine | 10.76 |
| Alanine | 12.14 |
| Cystine | 3.52 |
| Valine | 14.01 |
| Methionine | 0 |
| Isoleucine | 2.99 |
| Leucine | 4.73 |
| Tyrosine | 1.51 |
| Phenylalanine | 2.86 |
| Tryptophan | 2.03 |
| Lysine | 3.78 |
| Histidine | 2.47 |
| Arginine | 0 |

12. N-terminal amino acid

Alamine is detected by a DNP-forming method.

13. Stability to protease

When it was reacted with trypsin, α-chemotrypsin, papain, thermolysin, peptidase, alkalineprotease and pronase at a pH of 7.5 at 30° C. for 1 hour, no reduction in antibacterial activity was noted.

14. Stability to pH, temperature and light

It is relatively stable at a pH range of from 5 to 9, but rapidly loses its activity in strong acidity and strong alkalinity. On standing at room temperature, its activity decreases gradually. Its activity is lost almost entirely on exposure to ultraviolet light for several minutes.

15. Antibacterial action

Table 2 shows that it strongly inhibits Gram-positive bacteria and Gram-negative bacteria.

TABLE 2

Antimicrobial spectrum

| Test organism | Minimum inhibitory concentration ($\mu g/ml$) |
|---|---|
| Staphylococcus aureus 209P | 0.1 |
| Staphylococcus aureus Smith | 0.1 |
| Micrococcus flavus FDA16 | 0.05 |
| Sarcina lutea PCI 1001 | 0.1 |
| Bacillus anthracis | 0.2 |
| Bacillus subtilis NRRL 558 | 0.2 |
| Bacillus subtilis PCI 219 | 0.1 |
| Bacillus cereus | 0.2 |
| Escherichia coli NIHJ | 3.12 |
| Escherichia coli K-12 | 6.25 |
| Shigella dysenteriae | 1.56 |
| Shigella flexneri 46JS 11811 | 6.25 |
| Salmonella enteritidis 1891 | 25 |
| Proteus vulgaris OX-19 | 3.12 |
| Proteus rettgeri GN 311 | 6.25 |
| Proteus rettgeri GN 466 | 0.78 |
| Serratia marcescens | 50 |
| Pseudomonas aeruginosa A3 | >100 |
| Klebsiella pneumoniae PCI 602 | 3.12 |
| Mycobacterium 607 (*) | 3.12 |
| Mycobacterium phlei (*) | 3.12 |
| Candida albicans 3147 strain (**) | >100 |

(*) On a nutrient agar containing 1% of glycerol.
(**) On a nutrient agar containing 1% of glucose.

A nutrient agar was used for the others.

16. Anti-transplanted tumor activity and acute toxicity

It is effective against Ehrlich ascites carcinoma and ascites sarcoma 180 in mice when intraperiotoneally administered for 5 consecutive days in a dose of 0.01 to 1.0 mg/kg/day. At a optimal dosage of 0.025 to 0.25 mg/kg/day, the mice survive for more than 60 days. It is also effective against L1210 leukemia in mice when intraperitoneally administered for 5 consecutive days in a dose of 0.03 to 1.0 mg/kg/day, and it shows a maximum increase of lifespan of 148%. Its $LD_{50}$ in one intravenous injection to mice is 2.5 to 3.5 mg/kg.

It is noteworthy as described above that auromomycin strongly inhibits Gram-positive and Gram-negative bacteria, and in tiny amounts, has an anti-transplanted tumor activity.

The substance of this invention is most similar to macromomycin (U.S. Pat. No. 3,595,954) among proteinous anti-transplanted tumor antibiotics, but is a new substance having evidently different properties from macromomycin. To emphasize this, the characteristic differences between them in physicochemical and biological properties are summarized in Table 3.

TABLE 3

| Comparison of the characteristics of auromomycin with those of macromomycin | | |
|---|---|---|
| | Auromomycin | Macromomycin |
| Property of purified product | Yellow plate-like crystals | White powder |
| λ max($E_1{}_{cm}^{1\%}$) in the UV absorption spectrum | 273 mμ (13.3) and 357 mμ (4.6) | 280 mμ (6.5) |
| Valley of | 280 mμ and | 280 mμ |

TABLE 3-continued

Comparison of the characteristics of auromomycin with those of macromomycin

| | Auromomycin | Macromomycin |
|---|---|---|
| ORD spectrum | 350 mµ | |
| Antibacterial activity | Inhibits Gram-positive and Gram-negative bacteria. | Inhibits Gram-positive bacteria. |
| Antitumor activity effective dose against L1210 leukemia | 0.03–1.0 mg/kg/day, administered for 5 days | 0.2–10 mg/kg/day, administered for 5 days |
| $LD_{50}$ (one intravenous administration to mice) | 2.5–3.5 mg/kg | 25–50 mg/kg |

Furthermore, auromomycin differs in constituent amino acids from neocarcinostatin (J. Antibiotics, Ser. A, Tokyo, 18(2), 68–76 (1965)), a typical proteinous anti-transplanted tumor antibiotic.

Specifically, auromomycin does not contain arginine, but neocarcinostatin contains arginine but not histidine contained in auromomycin. Furthermore, auromomycin shows clear differences from such properties of neocarcinostatin as isoelectric point (pH 3.5) and antibacterial activity (inhibiting only Grampositive bacteria).

DESCRIPTION OF THE PREFERRED EMBODIMENTS

Examples are given below.

EXAMPLE 1

A culture medium was prepared which contained 1% of glucose, 1% of soluble starch, 1.5% of soybean powder (Esusan Meat, a product of Ajinomoto Co., Ltd.), 0.1% of dipotassium phosphate, 0.3% of sodium chloride, 0.1% of magnesium sulfate, 0.0007% of copper sulfate, 0.0001% of ferrous sulfate, 0.0008% of manganese chloride, 0.0002% of zinc sulfate and 0.05% of an antifoamer (Disfoam CC-118, a product of Nippon Oils and Fats, Co., Ltd.). The pH of this medium was adjusted to 7.2 by using 10% sodium hydroxide. Four 30-liter jar fermentors were each charged with 18 liters of the culture medium, and sterilized at 120° C. for 30 minutes. For seed culture, 100 ml of the same culture medium as above was placed in a 500 ml Sakaguchi flask, and sterilized at 120° C. for 30 minutes.

*Streptomyces macromomyceticus* was inoculated into the sterilized medium from an agar slant culture by platinum loop and cultivated at 28° C. for 2 days on a reciprocal shaker. Then, 90 ml of the resulting seed culture broth was inoculated into each of the jar fermentors, and the fermentation proceeded under aeration of 18 liters sterile air per minute with stirring at 500 rpm at 28° C. for 3 days. Thus, 16 liters of the fermentation broth was obtained per fermentor. 1.3 kg of a filtration aid (Dicalite 4159) was added to the fermentation broths in four fermentors (a total of 64 liters), and simultaneously 15% hydrogen peroxide was added. The mixture was filtered by a filter press. During the filtration, 15% hydrogen peroxide was continuously added in a total amount of 1.3 liters. To 53 liters of the resulting filtrate was added 37 kg of ammonium sulfate.

After dissolving, the solution was allowed to stand at 5° C. for 4 hours. 600 ml of an aqueous solution containing 265 g of anhydrous sodium carbonate was added to the solution, and immediately then, 600 ml of an aqueous solution containing 265 g of ferric chloride hexahydrate was added. The resulting precipitate was collected by centrifugal separation continuously at 5° C. and 10,000 rpm. 2.2 kg of the precipitate obtained was dissolved in 13 liters of deionized water. The water-insoluble matter was removed by continuous centrifugal separation at 5° C. and 10,000 rpm to obtain 12.1 liters of a supernatant liquid containing auromomycin. The solution was then passed through a column filled with 3 liters of Amberlite IRA-93 (Cl type) to afford 13.2 liters of an effluent. The effluent was concentrated to a volume of 200 ml by ultrafiltration using Ultra Filter UH-1 (a product of Toyo Filter Paper Co., Ltd.). A turbid matter which slightly formed was removed by centrifugal separation at 5° C. and 10,000 rpm. The resulting supernatant liquid was chromatographed on a column filled with 5 liters of Sephadex G-50 using deionized water as a developer to afford 400 ml of an active fraction.

Ammonium sulfate (80 g) was added to this solution, and after dissolving, the solution was passed through a column filled with 300 ml of Octyl Sepharose CL-4B. The column was subsequently eluted with a 35% saturated aqueous solution of ammonium sulfate, whereupon 600 ml of a yellow active fraction containing auromomycin was obtained after a peak of impure proteins. This fraction was fully desalted with Ultra Filter UH-1. 600 ml of the desalted solution was passed through a column of 300 ml DEAE-Sephadex A-25 (OH type), and the column was eluted with a 0.2 M tris-HCl buffer (pH 7.0). 180 ml of the active fraction was concentrated with Ultra Filter UH-1 to a volume of 70 ml. The solution was added to a column filled with 2 liters of Sephadex G-50, and chromatographed with deionized water as a developer to afford 150 ml of an active fraction. This solution was concentrated to a volume of 20 ml by using Ultra Filter UH-1. To the concentrate was gradually added 2.7 g of ammonium sulfate. The mixture was allowed to stand in a dark place at 5° C. for 3 to 4 days, whereupon yellow plate-like crystals precipitated. The mother liquor was almost colorless.

The crystals were collected on a glass filter, washed with 10 ml of a 15% aqueous solution of ammonium sulfate, and dissolved in 10 ml of deionized water. The solution was passed through a column filled with 200 ml of Sephadex G-25 to afford 15 ml of an active fraction. The fraction was lyophilized to afford 430 mg of a yellow powder. The yield of the antibacterial activity of the resulting yellow powder based on the cultivation broth filtrate was 3.5%.

EXAMPLE 2

In the same way as in Example 1, the microorganism was cultivated in four jar fermentors and a precipitate was obtained from the fermentation broth filtrate by salting out.

An aqueous solution of the precipitate was passed through Amberlite IRA-93 (Cl type), and the effluent was concentrated by using Ultra Filter UH-1. The concentrate was added to a column filled with 5 liters of Sephadex G-50, and chromatographed with deionized water as a developer to afford 380 ml of an active fraction.

Ammonium sulfate (90 g) was added to this fraction so that the concentration of ammonium sulfate was 40% saturation. After dissolving, the solution was passed through a column filled with 400 ml of Phenyl Sepharose CL-4B. The column was eluted by gradiently flowing aqueous solutions of ammonium sulfate from 40% saturation to 10% saturation. Thus, 400 ml of an active fraction was obtained.

It was concentrated to 100 ml with Ultra Filter UH-1. The concentrate was added to a column filled with 2.5 liters of Sephadex G-50, and chromatographed with deionized water. The resulting active fraction (200 ml) was concentrated with Ultra Filter UH-1 to 20 ml. Subsequently, in the same way as in Example 1, ammonium sulfate was added to precipitate yellow crystals, which were dissolved in deionized water. The solution was desalted with Sephadex G-25. The resulting active fraction was lyophilized to afford 380 mg of a yellow powder.

The yield of the antibacterial activity of the resulting yellow powder based on the cultivation broth filtrate was 3.3%.

We claim:

1. An antitumor antibiotic effective against transplanted tumors, auromomycin, having the following properties:
    (a) it crystallizes as yellow plate-like crystals;
    (b) it inhibits *Staphylococcus aureus*, *Bacillus subtilis*, *Sarcina lutea*, *Escherichia coli*, *Proteus rettgeri* and *Klebsiella pneumoniae* and inhibits the growth of Ehrlich ascites carcinoma, ascites sarcoma 180 and L1210 leukemia in mice;
    (c) it is readily soluble in water but insoluble in organic solvents;
    (d) its ultraviolet absorption spectrum shows an absorption maximum at 270–275 mµ and 350–360 mµ in a neutral to acidic aqueous solution and at 270–275 mµ and 340 mµ in an alkaline aqueous solution, and in any of these solutions, the spectrum has a shoulder at 290 mµ;
    (e) its infrated absorption spectrum has main absorption bands at 3300, 2980, 1650, 1540, 1460, 1400, and 1240 cm$^{-1}$, and slight absorptions at 3100, 1160, 1100 and 930 cm$^{-1}$;
    (f) it does not show a definite melting point nor a definite decomposition point, browns and carbonizes while foaming, and carbonizes completely at 260° C;
    (g) it shows a $[\alpha]_D^{20}$ of $-280°$ in 1% aqueous solution;
    (h) its optical rotatory dispersion spectrum in aqueous solution shows a valley at 280 mµ and 350 mµ;
    (i) it decolorizes a potassium permanganate solution, is positive in Folin-Lowry, xanthoproteic, Ehrlich, biuret, and ninhydrin reactions and is negative in phenol sulfuric acid, anthrone, orcinol, Elson-Morgan, and Molisch reactions;
    (j) it has an isoelectric point of pH 5.4;
    (k) its elementary analysis values are carbon 47.06%, hydrogen 6.62%, nitrogen 14.66%, sulfur 3.25% and oxygen 25.80%;
    (l) its molecular weight, as measured by a gel filtration method, is about 12,500;
    (m) the amino acids detected by its hydrolysis are aspartic acid, threonine, serine, glutamic acid, proline, glycine, alanine, cystine, valine, isoleucine, leucine, tyrosine, phenylalanine, tryptophan, lysine and histidine;
    (n) its N-terminal is alanine; and
    (o) the pH range over which it is stable in aqueous solution is 5 to 9.

* * * * *

UNITED STATES PATENT AND TRADEMARK OFFICE
CERTIFICATE OF CORRECTION

PATENT NO. : 4,259,319
DATED : March 31, 1981
INVENTOR(S) : UMEZAWA ET AL

It is certified that error appears in the above-identified patent and that said Letters Patent are hereby corrected as shown below:

Abstract, line 6: change "Sephalose" to --Sepharose--.

Column 1, line 19: change the word "macromoceticus" (in italics) to --macromomyceticus-- (in italics).

Column 1, line 60: change "microbilogical" to --microbiological--

Column 2, line 45: change "centrifufal" to --centrifugal--.

Column 3, line 34: change "Sephalose" to --Sepharose--.

Column 10, line 5: change "infrated" to --infrared--.

Signed and Sealed this

Eighth Day of September 1981

[SEAL]

Attest:

GERALD J. MOSSINGHOFF

Attesting Officer

Commissioner of Patents and Trademarks